(12) United States Patent
Kolesnick et al.

(10) Patent No.: US 6,274,309 B1
(45) Date of Patent: *Aug. 14, 2001

(54) METHOD FOR THE MODULATION OF ACID-SPHINGOMYELINASE-RELATED APOPTOSIS

(76) Inventors: Richard Kolesnick, 343 E. 74th St., New York, NY (US) 10021; Edward H. Schuchman, 3001 Lakeshore Dr., Haworth, NJ (US) 07641

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/687,707

(22) Filed: Jul. 26, 1996

(51) Int. Cl.$^7$ .............................. C12Q 1/02; C12Q 1/18; C12Q 1/42; C12Q 1/68

(52) U.S. Cl. ................................ 435/6; 424/9.2; 435/18; 435/19; 435/21; 435/29; 435/32; 436/63; 436/71; 800/3

(58) Field of Search .................................. 435/6, 18, 29, 435/172.3, 19, 21, 32; 436/63, 71; 424/9.2; 800/3

(56) References Cited

U.S. PATENT DOCUMENTS

| | | | |
|---|---|---|---|
| 5,500,432 | * 3/1996 | Nicolaou et al. | 514/281 |
| 5,583,160 | * 12/1996 | Igarashi et al. | 514/669 |
| 5,631,394 | * 5/1997 | Wei et al. | 556/404 |
| 5,637,486 | * 6/1997 | Tomei et al. | 435/172.1 |
| 5,874,235 | * 2/1999 | Chan et al. | 435/18 |

OTHER PUBLICATIONS

Santana, P. et al., 1996, "Acid Sphingomyelinase–deficient human lymphoblasts and mice are defective in radiation–induced apoptosis", Cell 86(2):189–199.*

Schissel et al., 1996,"Zn$^{2+}$ –stimulated Sphingomyelinase Is Secreted by Many Cell Types and is a Product of the Acid Sphingomyelinase Gene", J. Biol. Chem. 272(77).*

Verheij, M. et al., 1996, "Requirement for ceramide–initiated SAPK/JNK signaling in stress–induced apoptosis", Nature 380:75–77.*

Boucher, L.M. et al., 1995, "CD28 Signals through Acidic Sphingomyelinase", J. Exp. Med. 181:2059–2068.*

Cifone, M.G. et al., 1995, "Multiple pathways originate at the Fas/APO–1 (CD95) receptor: sequential involvement of phosphatidylcholine–specific phospholipase C and acidic sphingomyelinase in the propogation of the apoptotic signal", EMBO J. 14:5859–5868.*

Fuks, Z. et al, 1995, "Intravenous Basic Fibroblast Growth Factor Protects the Lung but not Mediastinal Organs Against Radiation–Induced Apoptosis in Vivo", Cancer J. 1:62–72.*

Jarvis et al, 1996, "Ceramide and the Induction of Apoptosis", Clin. Cancer Res. 2:1–6.*

Gulbins, E., 1995, "FAS–Induced Apoptosis Is Mediated Via a Ceramide–Initiated RAS Signaling Pathway", Immunity 2:341–351.*

Hannun, Y.A. & Obeid, L.M., 1995, "Ceramide: an intracellular signal for apoptosis", Trends Biochem. Sci. 20:73–77.*

Horinouchi, K. et al., 1995, "Acid sphingomyelinase deficient mice: a model of types A and B Niemann–Pick disease", Nature Genetics 10:288–293.*

Liu, P. & Anderson, R.G.W. et al., 1995, "Compartmentalized Production of Ceramide at the Cell Surface", *J. Biol. Chem.* 270:2719–27185.*

Otterbach, B. & Stoffel, W., 1995, "Acid Sphingomyelinase–Deficient Mice Mimic the Neurovisceral Form of Human Lysosomal Storage Disease (Niemann–Pick Disease)", Cell 811053–1061.*

Pushkareva, M., 1995, "Ceramide: an endogenous regulator of apoptosis and growth suppression", Imm. Today 16:294–297.*

Tepper, C.G. et al., 1995, "Role for ceramide as an endogenous mediator of Fas–induced cytotoxicity", PNAS USA 92:8443–8447.*

Yeyati, P.L. et al., 1995, "Fluorescence–Based Selection of Retrovirally Transduced Cells in the Absence of a marker Gene: Direct selection of Transduced Type B Niemann–Pick Disease Celles and Evidence for Bystander Correction", Human Gene Therapy 6:975–983.*

Fuks, Z. et al., 1994, "Basic Fibroblast Growth Factor Protects Endothelial Cells against Radiation–induced Programmed Cell Death in Vitro and in Vivo", Cancer Res. 54:2582–2590.*

Halmovitz–Friedman, A. et al., 1994, "Ionizing Radiation Acts on Cellular Membranes to Generate Ceramide and Initiate Apoptosis", J. Exp. Med. 180:525–535.*

Jarvis, W.D. et al., 1994, "Induction of apoptotic DNA damage and cell death by activation of the sphingomyelin pathway", PNAS USA 91:73–77.*

Kolesnick, R. & Golde, D.W., 1994, "The sphingomyelin pathway in tumor necrosis factor and interleukin–1 signaling", Cell 77(3):325–328.*

(List continued on next page.)

Primary Examiner—David Saunders
(74) Attorney, Agent, or Firm—Pennie & Edmonds LLP

(57) ABSTRACT

The present invention relates, first, to methods and compositions for the modulation of acid sphingomyelinase (ASM)-related processes, including apoptosis. Such apoptosis can include, but is not limited to, environmental stress-induced apoptosis such as, for example, ionizing radiation and/or chemotherapeutic agent-induced apoptosis. Apoptosis can be characterized by a cellular morphology comprising cellular condensation, nuclear condensation or zeiosis. The present invention further relates to methods for the identification of compounds which modulate (i.e., either increase or decrease) sensitivity to ASM-related processes, including apoptosis.

9 Claims, 8 Drawing Sheets

OTHER PUBLICATIONS

Figure 1A:
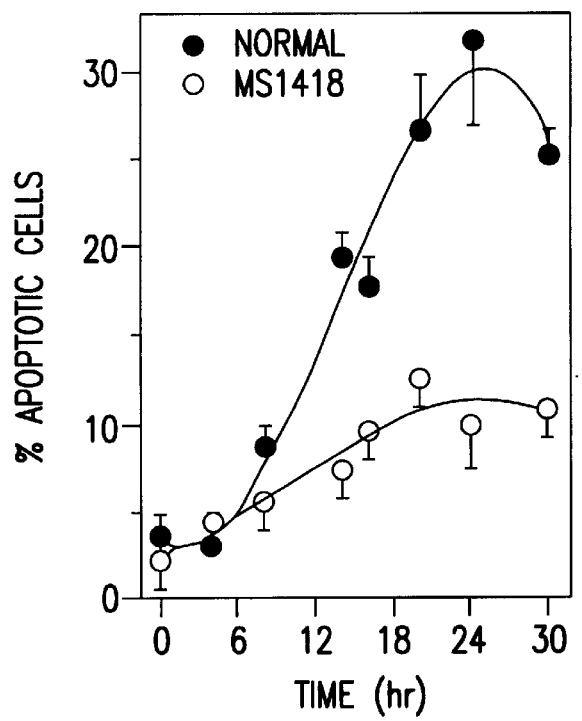

Okazaki, T. et al., 1994, "Characteristics and Partial Purification of a Novel Cytosolic, Magnesium–independent, Neutral Sphingomyelinase Activated in the Early Signal Transduction of 1α,25–Dihydroxyvitamin $D_3$–induced HL–60 Cell Differentiation", J. Biol. Chem. 269:4070–4077.*

Strasser, A. et al., 1994, "DNA Damage Can Induce Apoptosis in Proliferating Lymphoid Cells via p53–Independent Mechanisms Inhibitable by Bcl–2", Cell 79:329–339.*

Weigman, K. et al., 1994, "Functional Dichotomy of Neutral and Acidic Sphingomyelinases in Tumor Necrosis Factor Signaling", Cell 78:1005–1015.*

Cifone, et al., 1993, "Apoptotic Signaling through CD95 (Fas/Apo–1) Activates an Acidic Sphingomyelinase", J. Exp. Med. 177:1547–1552.*

Horinouchi, K. et al., 1993, "Mouse Models of Niemann–Pick Disease: Mutation Analysis and Chromosomal Mapping Rule Out the Type A and B Forms", Genomics 18:450–451.*

Lowe, S.W. et al., 1993, "p53–Dependent Apoptosis Modulates the Cytotoxicity of Anticancer Agents", Cell 74:957–967.*

Mathias, S. et al., 1993, "Activation of the Sphingomyelin Signaling Pathway in Intact EL4 Cells and in a Cell–Free System by IL–1β", Science 259:519–522.*

Obeid, L.M. et al., 1993, "Programmed Cell Death Induced by Ceramide", Science 259:1769–1771.*

Wood, S.A. et al., 1993, "Simple and efficient production of embryonic stem cell–embryo chimeras by coculture", PNAS USA 90:4582–4584.*

Schuchman, E.H. et al., 1992, "Structural Organization and Complete Nucleotide Sequence of the Gene Encoding Human Acid Sphingomyelinase (SMPD1)", Genomics 12:197–205.*

Suchi, M. et al., 1992, "Retroviral–mediated transfer of the human acid sphingomyelinase cDNA: Correction of the metabolic defect in cultured Niemann–Pick disease cells", PNAS 89:3227–3231.*

Nerzwella, D. & Stoffel, W., 1992, "Molecular Cloning of the Acid Sphingomyelinase of the Mouse and the Organization and Complete Nucleotide Sequence of the Gene", Bio. Chem. 373:1233–1238.*

Kolesnick, R.N., 1991, "Sphingomyelin and Derivatives as Cellular Signals", Prog. Lipid. Res. 30:1–38.*

Levran et al., 1991, "Niemann–Pick disease: A frequent missense mutation in the acid sphingomyelinase gene of Ashkenazi Jewish type A and B patients", PNAS USA 88:37848–37852.*

Levran, O. et al., 1991, "Niemann–Pick Type B Disease", J. Clin. Invest. 88:806–810.*

Quintern, L.E. et al., 1991, "Human Acid Spingomyelinase from Human Urine", Meth. Enzymol. 197:536–540.*

Schuchman, E.H. et al., 1991, "Human Acid Sphingomyelinase", J. Biol. Chem. 266:8531–8539.*

Dressler, K. & Kolesnick, R.N., 1990, "Ceramide 1–Phosphate, a Novel Phospholipid in Human Leukemia (HL–60) Cells", J. Biol. Chem. 256:14917–14921.*

Maruyama, E.N. & Arima, M., 1989, "Purification and Characterization of Neutral and Acid Spingomyelinases from Rat Brain", J. Neurochem. 52:611–618.*

Okazaki, T. et al., 1989, "Sphingomyelin Turnover Induced by Vitamin $D^3$ in HL–60 Cells", J. Biol. Chem. 264:19076–19080.*

Van Veldhoven, P. et al., 1989, "Enzymatic Quantification of Sphingosine in the Picomole Range in Cultured Cells", Anal. Biochem. 183:177–189.*

Spence, W.M., 1989, "A New $Zn^{2+}$ –stimulated Sphingomyelinase in Fetal Bovine Serum", J. Biol. Chem. 264:5358–5364.*

Merrill, J.A.H. et al., 1988, "Quantitation of Free Sphingosine in Liver by High–Performance Liquid Chromatography", Anal. Biochem. 171:373–381.*

Gossler et al., 1986, "Transgenesis by means of blastocyst–derived embryonic stem cell lines", PNAS USA 83:9065–9069.*

Robertson et al., 1986, "Germ–line transmission of genes introduced into cultured pluripotential cells by retroviral vector", Nature 322:445–448.*

Bradley, O. et al., 1984, "Formation of germ–line chimeras from embryo–derived teratocarcinoma cell lines", Nature 309:255–258.*

Evans, M.J. et al., 1981, "Establishment in culture of pluripotential cells from mouse embryos", Nature 292:154–156.*

Yedger, S. & Gatt, S., 1976, "Effect of Triton X–100 on the Hydrolysis of Sphingomyelin by Sphingomyelinase of Rat Brain", Biochemistry 15:2570–2573.*

Godman, G.C. et al., 1975, "Action of Cytochalasin D on Cells of Established Lines", J. Cell Biol. 64:644–667.*

Rao, B.G. & Spence, M.W., 1967, "Sphingomyelinase activity at pH 7.4 in human brain and a comparison to activity at pH 5.0", J. Lipid Res. 17:506–515.*

Schneider, P.B. & Kennedy, E.P., 1967, "Sphingomyelinase in normal human spleens and in spleens from subjects with Niemann–Pick disease", J. Lipid Res. 8:202–209.*

Brady, R.O. et al., 1966, "The Metabolism of Sphingomyelin, II. Evidence of an Enzymatic Deficiency in Niemann–Pick Disease", PNAS USA 55:366–369.*

Chen, J.P.S. et al., 1956, "Microdetermination of Phosphorus", Anal. Chem 28:1756–1758.*

* cited by examiner

| MICE | TISSUSES | 4 Gy | 5 Gy | 7.5 Gy |
|---|---|---|---|---|
| 129/SV | THYMUS | 558 (27.9%) | 652 (32.6%) | 737 (36.9%) |
| ASMASE -/- | | 240 (12.0%)* | 346 (17.3%)* | 565 (28.2%)* |
| 129/SV | SPLEEN | 288 (14.3%) | 470 (23.6%) | 560 (28.6%) |
| ASMASE -/- | | 185 (9.2%)* | 323 (16.1%)* | 397 (19.0%)* |

*p< 0.001_vs. 129/SV

METHOD FOR THE MODULATION OF ACID-SPHINGOMYELINASE-RELATED APOPTOSIS

1. INTRODUCTION

The present invention relates, first, to methods and compositions for the modulation of acid sphingomyelinase (ASM)-related processes, including apoptosis. Such apoptosis can include, but is not limited to, environmental stress-induced apoptosis such as, for example, ionizing radiation and/or chemotherapeutic agent-induced apoptosis. Apoptosis can be characterized by a cellular morphology comprising cellular condensation, nuclear condensation or zeiosis. The present invention further relates to methods for the identification of compounds which modulate (i.e., either increase or decrease) sensitivity to ASM-related processes, including apoptosis.

2. BACKGROUND

The sphingomyelin pathway is a ubiquitous, evolutionarily conserved signaling system initiated by hydrolysis of sphingomyelin to generate the second messenger ceramide. Two forms of sphingomyelinase, distinguishable by the pH optima, are capable of initiating signaling. Acid sphingomyelinase (pH optimum 4.5–5.0) was originally identified as a lysosomal hydrolase required for turnover of cellular membranes (for review see Kolesnick, R. N., 1991, Prog. Lipid Res. 30 1–38). However, Kronke and co-workers proposed that this enzyme was also targeted to the plasma membrane and signaled in response to activation of the 55 kD TNF receptor (Wiegmann, K. et al., 1994, Cell 78:1005–1015). Activation of acid sphingomyelinase has also now been associated with signaling via Fas, CD28 and the interleukin (IL)-1 receptor (Cifone, et al., 1993., J. Exp. Med. 177:1547–1552; Boucher, L.-M. et al., 1995, J. Exp. Med. 181:2059–2068.; Liu. P. & Anderson, R. G. W., et al., 1995, J. Biol. Chem. 270:27179–27185. Human acid sphingomyelinase is the product of a single gene, although alternative processing of the primary transcript allows for the generation of multiple forms (Schuchman, E. H., et al., 1991, J. Biol. Chem. 266:8531–8539; Schuchman, E. H., et al., 1992, Genomics 12:197–205. Inherited mutations of the human acid sphingomyelinase gene lead to enzyme deficiency and the genetic disorder known as Niemann Pick disease (NPD; Brady et al., R. O., et al., 1966, Proc. Natl. Acad. Sci. USA 55, 366–369.; Schneider, P. B. & Kennedy, E. P., 1967, J. Lipid Res. 8:202–209.

Neutral sphingomyelinase (pH optimum 7.4) was originally defined as a $Mg^{2+}$-dependent enzyme localized to the outer leaflet of the plasma membrane (Rao, B. G. & Spence, M. W., 1976, J. Lipid Res. 17:506–515.; Yedger, S. & Gatt, S., 1976. Biochemistry 15:2570–2573. However, a $Mg^{2+}$-independent isoform of neutral sphingomyelinase which localizes to the cytoplasm has recently been identified (Okazaki, T. et al., 1989, J. Biol. Chem. 264:19076–19080.; Okazaki, T. et al., 1994, J. Biol. Chem. 269:4070–4077.). The neutral sphingomyelinase has not yet been characterized at the molecular level.

Neutral sphingomyelinase activation has been demonstrated in response to cellular stimulation with TNFa (Wiegmann, K. et al., 1994, Cell 78:1005–1015) anti-Fas antibody (Tepper, C. G., et al., 1995, Proc. Natl. Acad. Sci. USA 92:8443–8447.; Cifone, M. G. et al., 1995, EMBO J. 14:5859–5868.), and vitamin D (Okazaki, T. et al., 1989, J. Biol. Chem. 264:19076–19080; Okazaki, T. et al., 1994, J. Biol. Chem. 269:4070–4077.). It has also been suggested that neutral sphingomyelinase signals in response to IL-1b (Mathias, S. et al., 1993, Science 259:519–522) and ionizing radiation (Halmovitz-Friedman, A. et al., 1994, J. Exp. Med. 180:525–535.).

Although ceramide has been implicated as the second messenger for a variety of stress stimuli including TNFa, Fas ligand, ionizing radiation, heat shock, ultraviolet light and oxidative stress (Obeid, L. M. et al., 1993, Science 259:1769–1771.; Cifone, M. G. et al., 1993, J. Exp. Med. 177:1547–1552.; Jarvis, W. D., et al., 1994, Proc. Natl. Acad. Sci. USA 91:73–77; Fuks, Z., et al., 1994, Cancer Res. 54:2582–2590; Halmovitz-Friedman, A., et al., 1994, J. Exp. Med. 180:525–535.; Gulbins, E. et al., 1995, Immunity 2:341–351.; Verheij, M. et al., 1996, Nature 380:75–79; Jarvis, W. D. et al., 1996, Clin. Cancer Res. 2:1–6). Evidence for such speculation has been circumstantial (Verheij, M. et al., 1996, Nature 380:75–79; Hannun, Y. A. & Obeid, L. M, 1995, Trends Biochem. Sci. 20:73–77). Definitive proof, therefore, that ceramide generation is a primary mediator of the apoptotic response is lacking.

3. SUMMARY OF THE INVENTION

The present invention relates, first, to methods and compositions for the modulation of acid sphingomyelinase (ASM)-related processes, including apoptosis. Such apoptosis can include, but is not limited to, environmental stress-induced apoptosis such as, for example, ionizing radiation and/or chemotherapeutic agent-induced apoptosis. Apoptosis can be characterized by a cellular morphology comprising cellular condensation, nuclear condensation or zeiosis.

The present invention is based, in part, on the surprising discovery, described in the Example presented in Section 6, below, that acid sphingomyelinase activity is required for activation of stress-induced apoptotic cellular pathways. Specifically, the data presented in these Examples shows that ASM-deficient cell lines and ASM-deficient animals are resistant to radiation-induced apoptosis. Thus, the data described herein define, for the first time, an obligatory role for ceramide generation in signalling of stress-induced apoptosis.

The present invention further relates to methods for the identification of compounds which modulate ASM-related processes, including apoptosis. "Modulation" as used herein, can refer, first, to an increase in the sensitivity of cells, specially neoplastic cells, to ASM-related processes, including apoptosis. Alternatively, "modulation" can refer to a decrease in the sensitivity of cells to ASM-related processes such as apoptosis; e.g., can refer to an increase in the cells' resistance to apoptosis.

Methods for the identification of compounds which increase a cell's sensitivity to ASM-related processes such as apoptosis can be performed to identify targets and compounds which mimic ASM or act downstream of ASM in apoptotic pathways. Among the compounds and targets identified via such identification methods are agents which can be utilized to increase a neoplastic cell's sensitivity to apoptosis, thereby improving the clinical effects of anti-cell proliferative therapy, e.g. radiation and/or chemotherapeutic therapies.

Such methods can include, for example, a method comprising, first contacting an acid sphingomyelinase-deficient cell with a test compound, exposing the cell to a stress stimulus for a time sufficient to induce apoptosis in a cell exhibiting normal acid sphingomyelinase activity. Second, an acid sphingomyelinase-deficient cell is exposed, in the absence of the test compound, to the stress stimulus for a time sufficient to induce apoptosis in a cell exhibiting normal acid sphingomyelinase activity. The exposed cells are monitored for the presence of an apoptotic morphology, such that if the cell exposed to the test compound exhibits a more severe apoptotic morphology, the test compound represents a compound which increases a cell's sensitivity to acid sphingomyelinase-related apoptosis.

Alternatively, such methods for identifying a compound which increases a cell's sensitivity to acid sphingomyelinase-related apoptosis can also comprise, first, contacting an acid sphingomyelinase-deficient cell with a test compound, and exposing the cell to a stress stimulus. Next, an acid sphingomyelinase-deficient cell is exposed, in the absence of the test compound, to the stress stimulus. The levels of sphingomyelin and ceramide present in the exposed cells are compared, such that if the level of sphingomyelin in the cell exposed in presence of test compound is less than that of the cell exposed in the absence of the test compound, or the level of ceramide in the cell exposed in the presence of test compound is greater than that of the cell exposed in the absence of test compound, the test compound represents a compound which increases a cell's sensitivity to acid sphingomyelinase-related apoptosis.

The cells utilized in the above-described methods for identifying compounds which increase a cell's sensitivity to ASM-related apoptosis can be part of a genetically engineered nonhuman animal deficient for the acid sphingomyelinase gene, such that the animal is exposed to the stress stimulus, either in the presence or absence of test compound.

Additionally, methods for the identification of compounds which decrease a cell's sensitivity to ASM-related processes such as apoptosis can be performed. Such screens can identify additional targets in the apoptotic pathway which, like ASM, are necessary for stress-induced apoptosis to occur. Further, such screens can identify compounds useful for minimizing the effects of stress-induced apoptosis, for example, apoptosis induced by radiation.

Such methods for identifying a compound which decreases a cell's sensitivity to acid sphingomyelinase-related apoptosis can include, for example, a method comprising, first, contacting a cell exhibiting acid sphingomyelinase activity with a test compound and exposing the cell to an apoptosis-inducing stress stimulus. Next, a cell which exhibits acid sphingomyelinase activity is exposed, in the absence of test compound, to the stress stimulus. The exposed cells are monitored for the presence of an apoptotic morphology, such that if the cell exposed in the presence of the test compound exhibits a less severe apoptotic morphology, than the cell exposed in the absence of the test compound, the test compound represents a compound which decreases a cell's sensitivity to acid sphingomyelinase-related apoptosis.

Such methods for identifying a compound which decreases a cell's sensitivity to acid sphingomyelinase-related apoptosis, can also include, for example, a method comprising, first, contacting a cell exhibiting acid sphingomyelinase activity with a test compound, and exposing the cell to a stress stimulus. Next, a cell exhibiting acid sphingomyelinase activity is exposed, in the absence of test compound, to the stress stimulus. The levels of sphingomyelin and ceramide present in the exposed-cells are compared such that if the level of sphingomyelin in the cell exposed in the presence of test compound is greater than that of the cell exposed in the absence of test compound, or the level of ceramide in the cell exposed in the presence of test compound, is less than that of the cell exposed in the absence of test compound, the test-compound represents a compound which decreases a cell's sensitivity to acid sphingomyelinase-related apoptosis.

In the above-described methods for identifying compounds which decrease a cell's sensitivity to ASM-related apoptosis, the cells utilized can be transgenic cells comprising cells deficient in endogenous acid sphingomyelinase gene activity and containing a functional human acid sphingomyelinase transgene capable of expressing functional human acid sphingomyelinase. Further, such cells can be part of genetically engineered nonhuman animal deficient in endogenous acid sphingomyelinase gene activity and containing integrated in its cells a functional human acid sphingomyelinase transgene capable of expressing functional human acid sphingomyelinase.

In the above-described methods for identifying compounds which decrease a cell's sensitivity to ASM-related apoptosis, the cells utilized can also be genetically engineered cells which exhibit a greater level of acid sphingomyelinase activity than non-genetically engineered cell of the same type.

4. BRIEF DESCRIPTION OF THE FIGURES

FIG. 1A. Normal lymphoblasts or MS1418 NPD lymphoblasts were irradiated with 20 Gy and incubated at 37° C. for the indicated times. Morphologic changes of nuclear apoptosis were quantified by staining with the DNA-specific fluorochrome bisbenzimide. Cells with condensation of chromatin, its compaction along the periphery of the nucleus, or segmentation of the nucleus into three or more chromatin fragments were considered apoptotic. A minimum of 500 cells were scored for the incidence of apoptosis. The data (mean+S.E.M.) represent two independent determinations from three separate experiments.

Figure 1B:
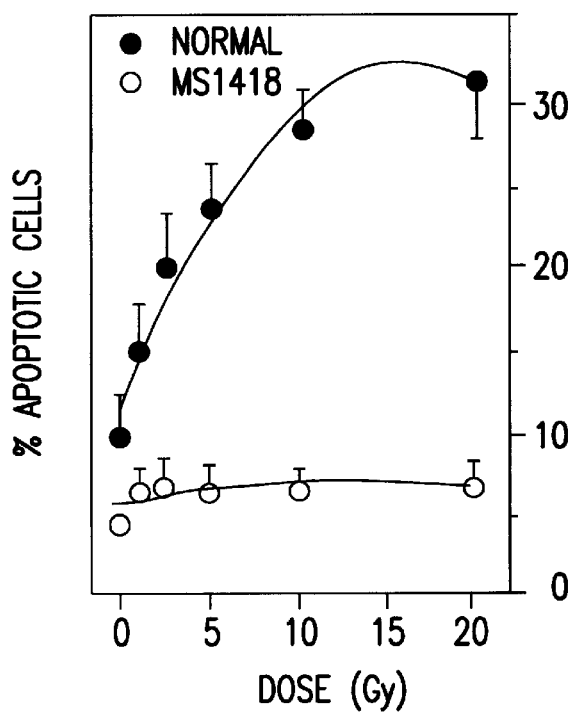

FIG. 1B. The dose-dependence of radiation-induced apoptosis was assessed in both types of lymphoblasts at 24 hours. Apoptotic cells were quantified as in FIG. 1A. The data (mean+S.E.M.) represent duplicate determinations from four separate experiments.

Figure 1C:
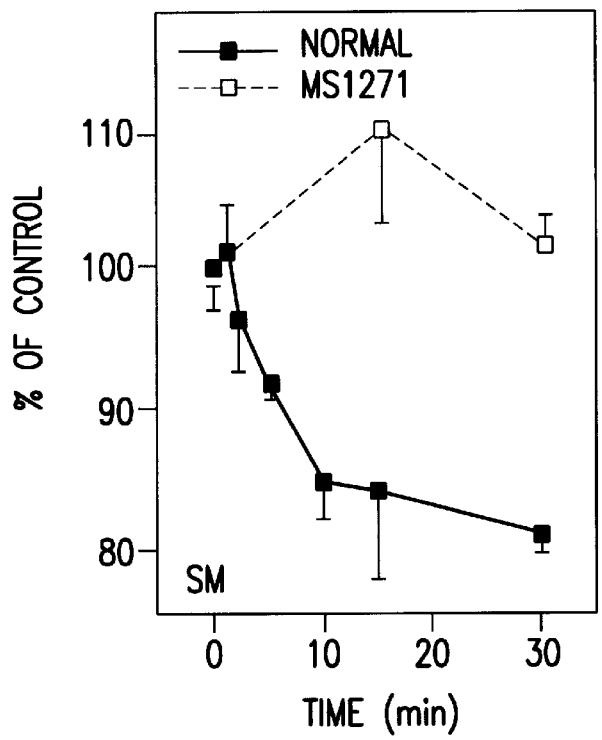

FIG. 1C. Normal or MS1271 NPD lymphoblasts were labeled to isotopic equilibrium with medium containing [3H]choline (1 mCi/ml), irradiated with 20 Gy, and incubated at 37° C. for the times indicated. Lipids were extracted with chloroform:methanol:1 NHCl (100:100:1, v/v/v), subjected to mild alkaline hydrolysis to remove glycerolipids, and sphingomyelin (SM) was resolved by thin-layer chromatography. Sphingomyelin levels were determined by lipid scintillation spectrometry. The values represent mean+ S.E.M. of independent triplicate determinations from two separate studies.

Figure 1D:
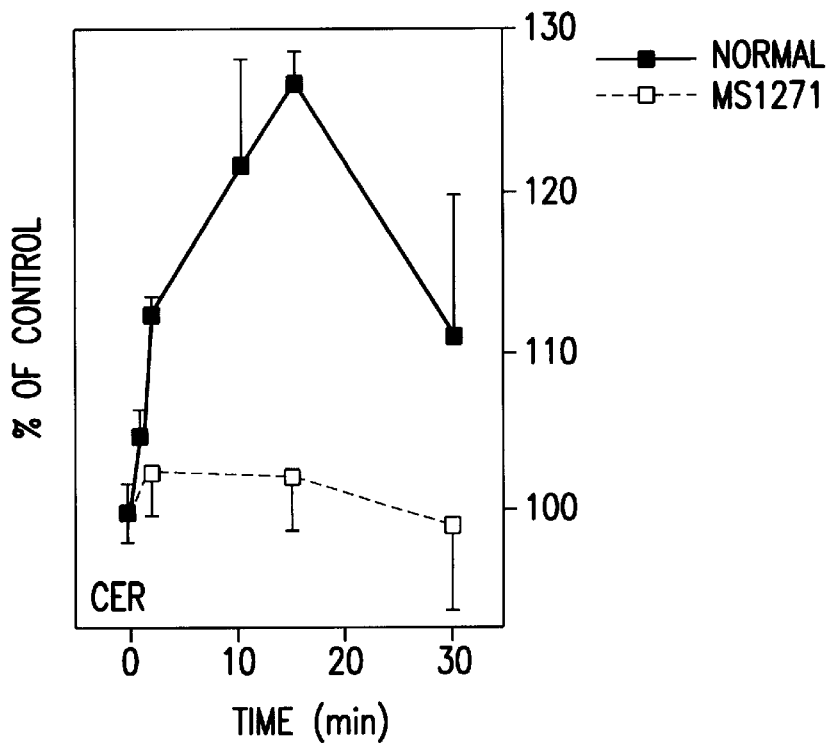

FIG. 1D. Unlabeled lymphoblasts were handled as in C and ceramide (Cer) levels were quantified by the diacylglycerol kinase assay as described in experimental procedures. The values represent mean+S.E.M. of independent triplicate determinations from three separate studies with control lymphoblasts and five experiments with MS1271 NPD lymphoblasts.

Figure 2A:
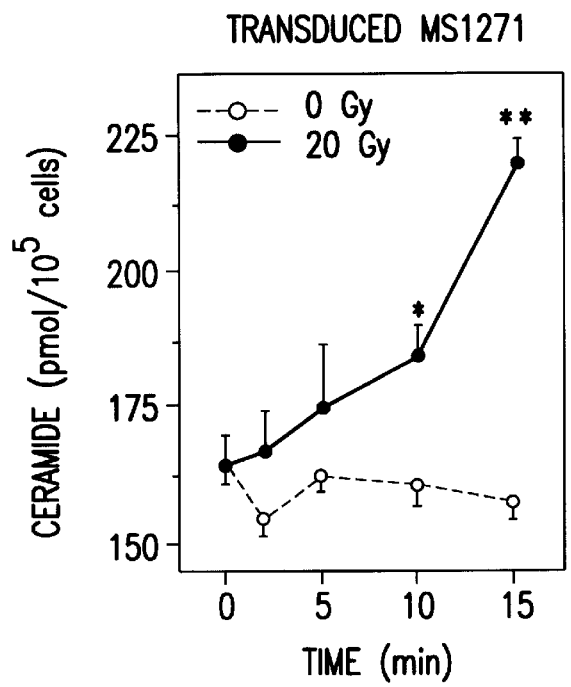

FIG. 2A. Retroviral transduction was performed by co-incubation for 48 hours with amphotropic packaging cell lines which secrete acid sphingomyelinase-containing retrovirus as described in the experimental procedures. MS1271 NPD lymphoblasts transduced with the acid sphingomyelinase CDNA were incubated for 24 hours in serum-free medium and then irradiated at 20 Gy. Ceramide levels were determined as in FIG. 1D at the times indicated. The data (mean+S.E.M.) represent 2 independent determinations from2 separate experiments. *p<0.05; **p<0.005.

Figure 2B:
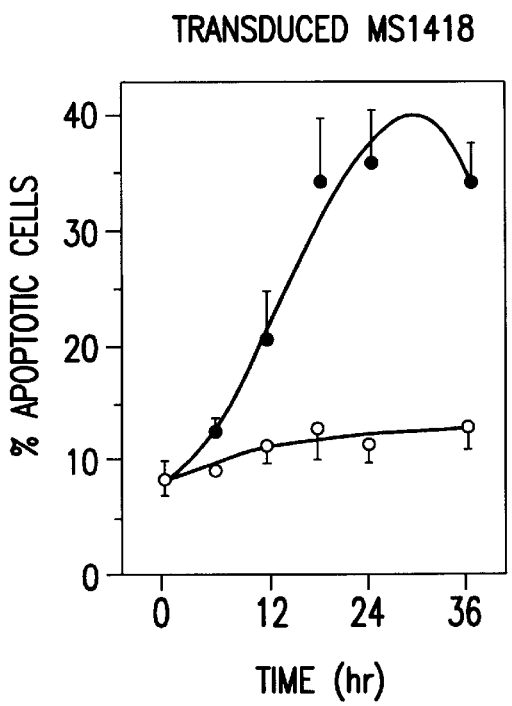
Figure 2C:
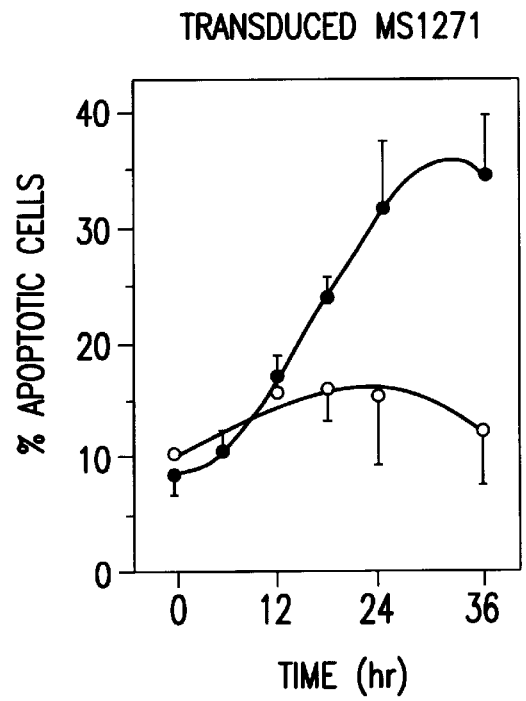

FIGS. 2B,C. NPD lymphoblasts were infected with acid sphingomyelinase-containing retrovirus as in A and irradiated with 20 Gy. Apoptosis was quantified by staining with bisbenzamide as in FIG. 1. Values represent the mean+ S.E.M. of independent determinations from 3 (MS1418) or 4 (MS1271) separate experiments.

Figure 3A:
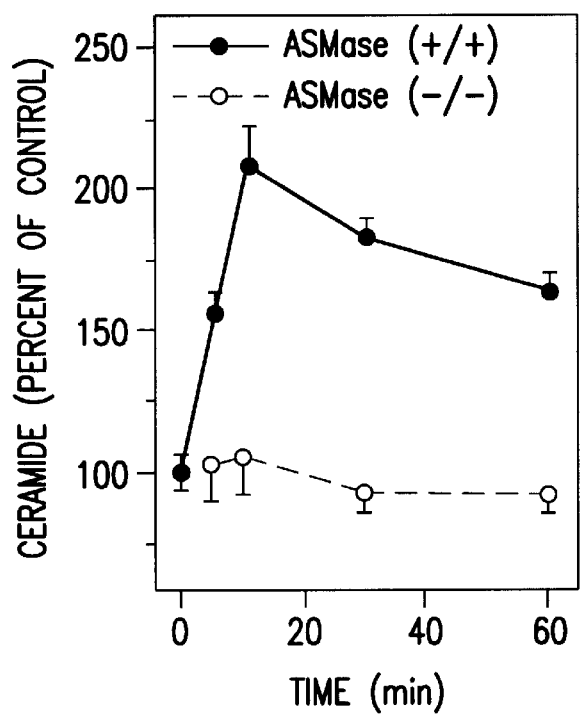

FIGS. 3A,B. Male 129/SV (Acid sphingomyelinase (ASMase) +/+) and knock-out (ASMase −/−) mice received whole body radiation at 10 Gy 3(A) or at varying doses for 30 min 3(B), and at the indicated times were sacrificed by cervical dislocation. The lungs were dissected, homogenized in 8 volumes (w/v) of ice-cold PBS, and lipids were extracted with chloroform:methanol (2:1, v/v). Ceramide levels were measured by fluorescence spectrometry after derivitization with o-phthaldehyde as described in experimental procedures. The values represent mean+S.E.M. of duplicate determinations from 2 separate experiments.

Figure 4:
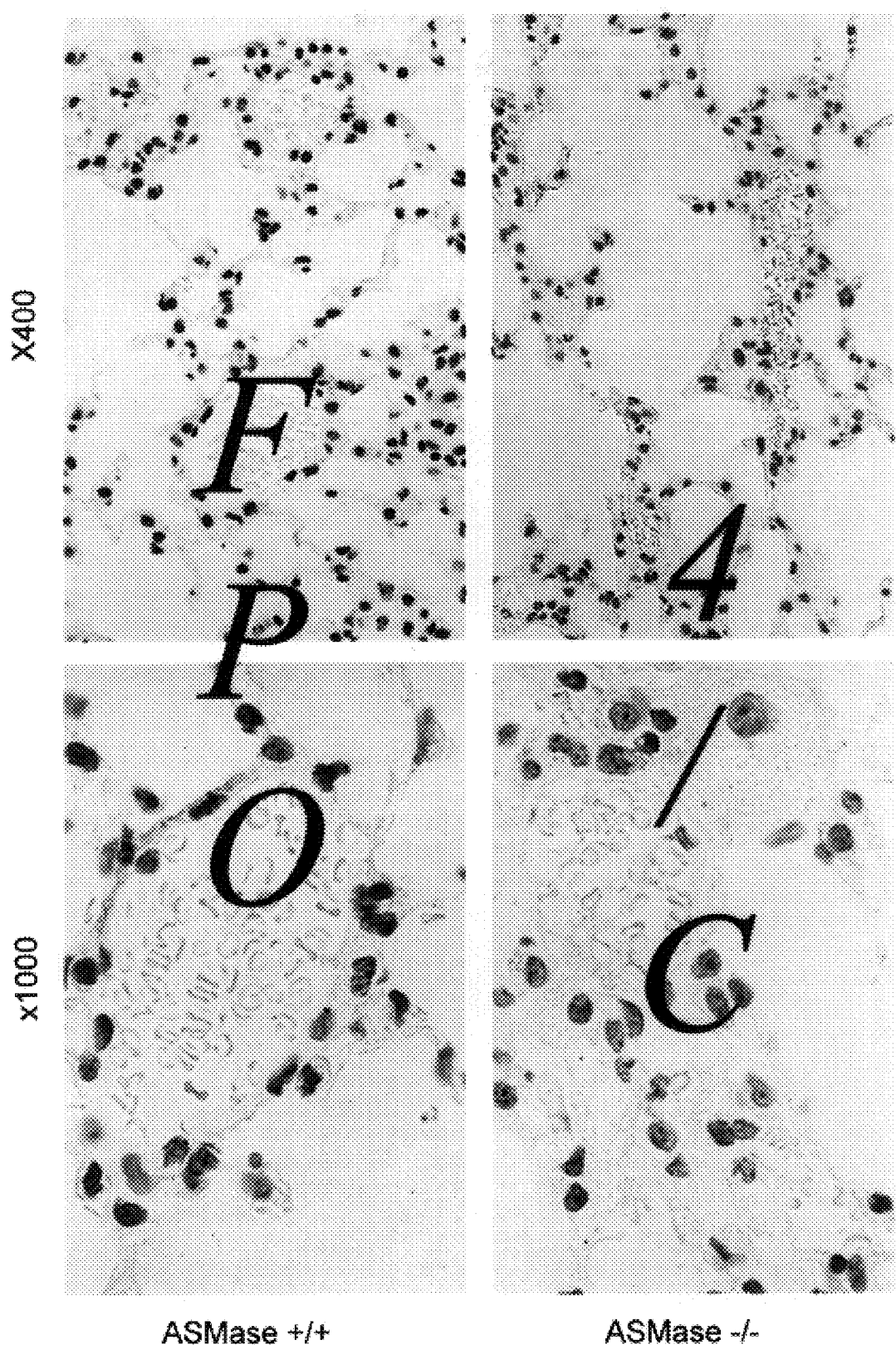

FIG. 4. Radiation induces apoptosis in lungs of 129/SV (acid sphingomyelinase +/+) but not in the knock-out (acid sphingomyelinase −/−) mice. Lung specimens from 129/SV (ASMase +/+) and knock-out (ASMase −/−) mice were obtained 10 hours after exposure to 20 Gy whole body irradiation Tissues were fixed in formalin, paraffin-embedded, and 5 micron sections were used for TUNEL assays. Apoptotic nuclei are identified by brown-yellow staining, a product of the diaminobenzidine chromogen used. In contrast, normal nuclei stain blue due to counter-staining with hematoxylin. Note the intense TUNEL signal in the nuclei of endothelial cells of small blood vessels and capillaries, and occasionally in alveolar pneumocytes in the lung of the 129/SV mouse (left upper and lower panels). The majority of capillaries and small blood vessels and all pneumocytes of the acid sphingomyelinase knock-out mice display negative TUNEL signals (right upper and lower panels). Original magnification: upper panel, x400; lower panel, x1000. This experiment represents one of four similar studies.

Figures 5A, 5B:
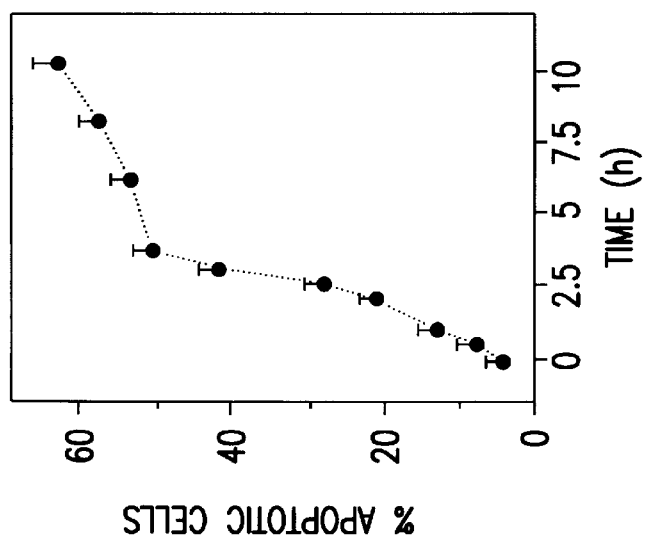

FIG. 5A. Radiation induces a time-dependent increase in apoptosis in the thymus of C3H/HeJ mice. C3H/HeJ mice received whole body radiation at 7.5 Gy and at the times indicated were sacrificed. Apoptosis in thymic tissue was measured by TUNEL assay as described in FIG. 4. A minimum of 1000 cells was scored for the incidence of apoptosis. The data (mean+range) represent duplicate determinations from one representative of three separate experiments.

FIG. 5B. Quantitation of radiation-induced apoptosis in thymic and splenic tissue from 129/SV (ASMase +/+) and knockout (ASMase −/−) mice. Two thousand cells were counted in four high power fields (x400). Numbers indicate apoptotic cells, and the percentage of apoptotic cells is shown in arentheses. Differences between 129/SV and ASMase −/− were evaluated by c2 and at each dose tested, P<0.001.

Figure 6:
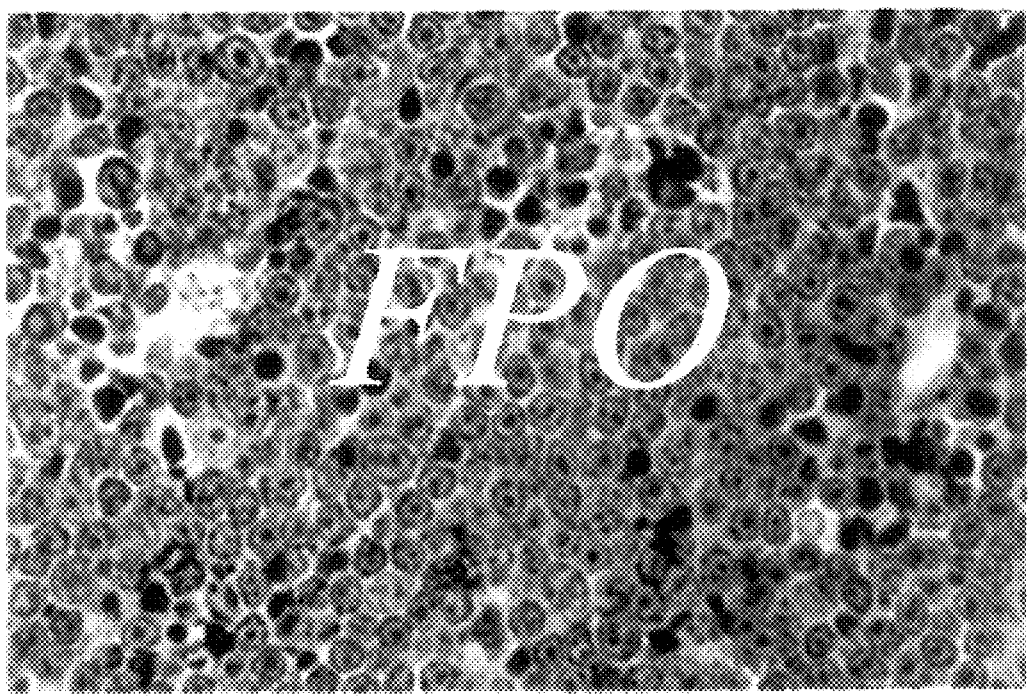
Figure 6:
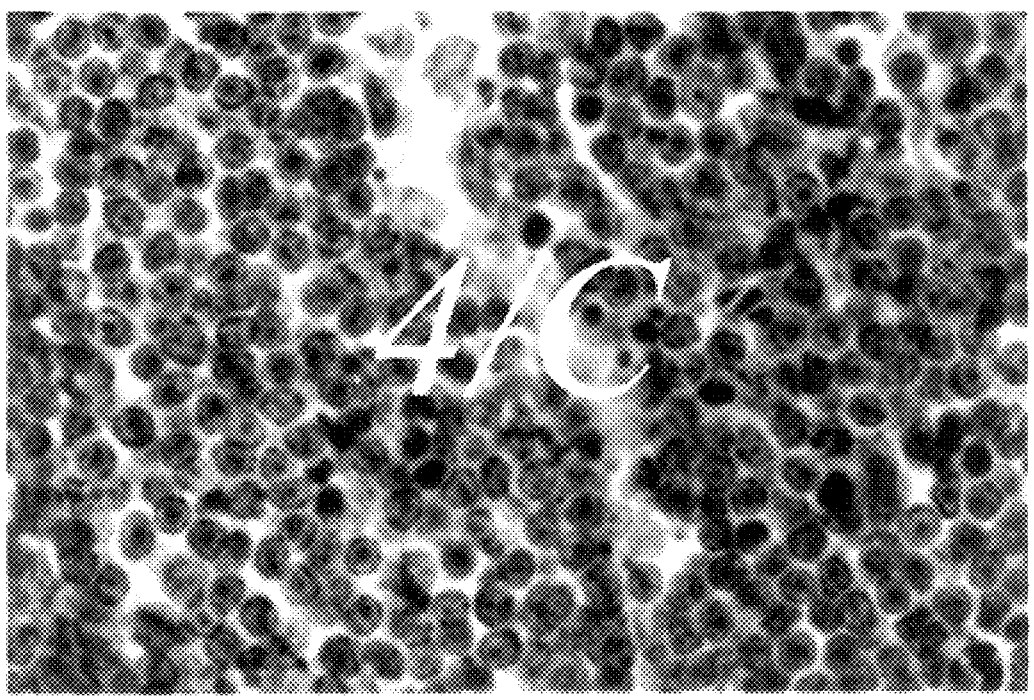

FIG. 6. Thymic samples from 129/SV (ASMase +/+) and knockout (ASMase −/−) mice were obtained 2.5 hours after exposure to 5 Gy whole body irradiation, and handled as in FIG. 4. Five micron sections were used for TUNEL assays, and apoptotic nuclei were identified as specified in FIG. 4. An intense TUNEL signal was noted in the nuclei of a proportion of thymocytes in the cortical region of 129/SV treated mice, occasionally forming small clusters of apoptotic cells (upper panel). In certain instances, TUNEL staining was identified as a dark brown-to-blue reaction due to nuclear condensation of cells undergoing apoptosis. The percentage of positive TUNEL thymocytes was reduced in the acid sphingomyelinase knock-out mice, in which cluster formation was rare and only scattered apoptotic cells were observed (lower panel). Original magnification: x400. This experiment represents one of three similar studies.

Figure 7:
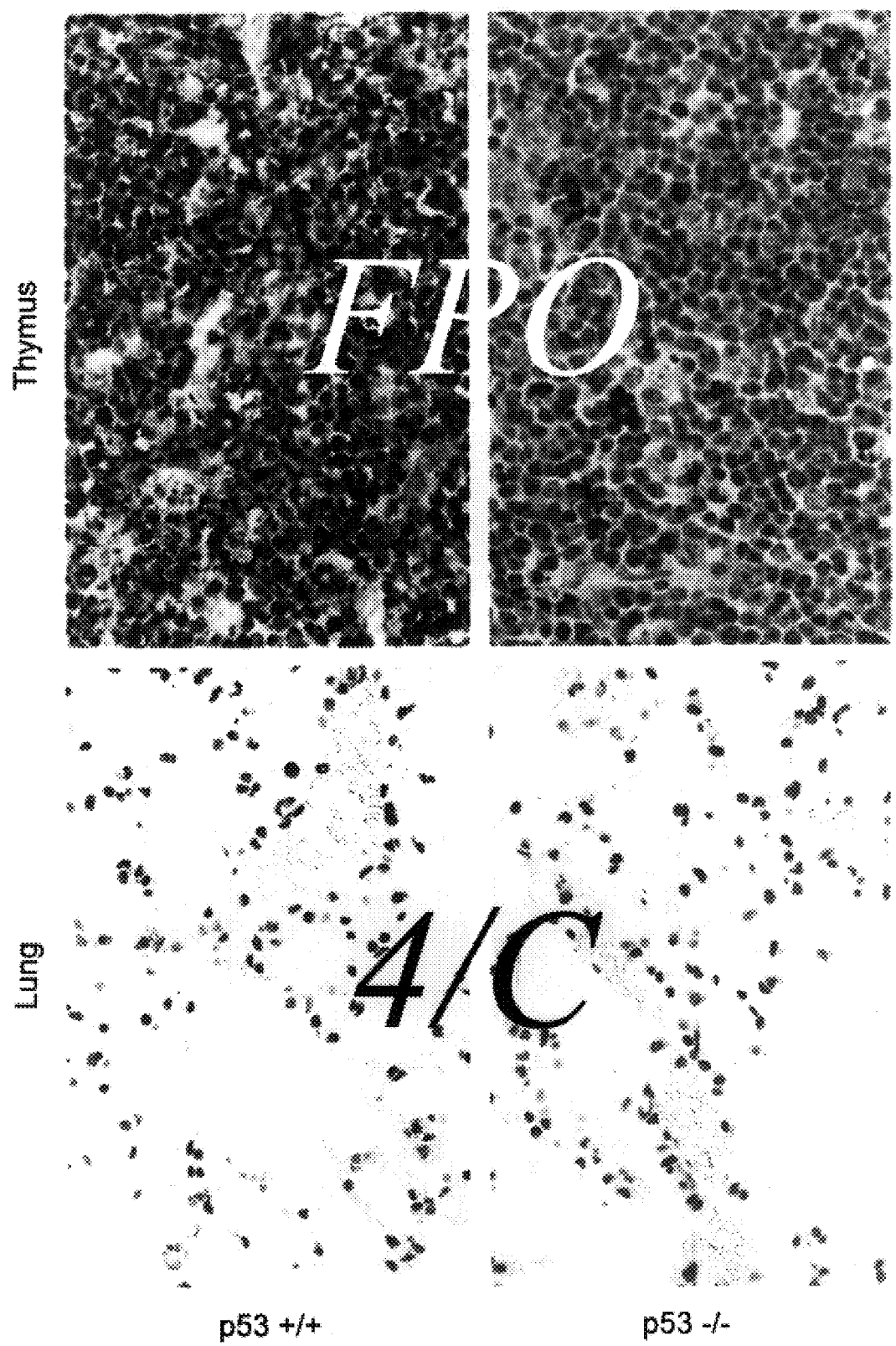

FIG. 7. Radiation-induced apoptosis in thymic (upper panel) and lung tissue (lower panel) of C57Bl/6 (p53+/+) and p53 knock-out (p53−/−) mice. Thymic specimens from C57Bl/6 (p53+/+) and p53 knock-out mice were obtained 10 hours after exposure to 20 Gy whole body irradiation, and handled as in FIG. 6 (upper panels; original magnification: x400). The lower panels show TUNEL stains of lung specimens obtained from the same mice (original magnification: x1000).

5. DETAILED DESCRIPTION OF THE INVENTION

5.1. Screening Assays for Compounds that Increase Sensitivity to ASM-Related Processes Described in this Section are screening methods for identifying compounds that are capable of increasing a cell's sensitivity to ASM-related processes, including apoptosis. Compounds identified very screens such as those described herein can be utilized, for example, as parts of methods for improving the clinical effects of radiation therapy, as discussed, below, in Section 5.4.

As demonstrated in the Examples presented in Section 6, below, stress-induced apoptosis is dependent upon the presence of ASM activity, identifying ASM as an upstream regulator of the apoptotic response. In order to identify compounds which act increase a cell's sensitivity to apoptosis, assays-can, for example, be conducted on ASM-deficient cells, cell lines and/or animals to identify targets and compounds which mimic ASM or act downstream of ASM in the apoptotic pathway.

Such assays can comprise exposing an ASM-deficient cell, cell line or animal to a stress stimulus such as radiation, for example, ionizing radiation, in either the presence or absence of a test compound. In instances wherein the presence of the test compound is accompanied by the appearance of apoptosis the test compound is to be considered one which increases a cell's sensitivity to ASM-related processes. It is preferable that the apoptosis observed in the presence of the test compound is more severe or more pronounced than that observed in 'stress-exposed ASM-deficient cells, cell lines or animals not exposed to the test compound.

Such methods can include, for example, a method comprising, first contacting an acid sphingomyelinase-deficient cell with a test compound, exposing the cell to a stress stimulus for a time sufficient to induce apoptosis in a cell exhibiting normal acid sphingomyelinase activity. Second, an acid sphingomyelinase-deficient cell is exposed, in the absence of the test compound, to the stress stimulus for a time sufficient to induce apoptosis in a cell exhibiting normal acid sphingomyelinase activity. The exposed cells are monitored for the presence of an apoptotic morphology, such that if the cell exposed to the test compound exhibits a more severe apoptotic morphology, the test compound represents a compound which increases a cell's sensitivity to acid sphingomyelinase-related apoptosis.

Alternatively, such methods for identifying a compound which increases a cell's sensitivity to acid sphingomyelinase-related apoptosis' can also comprise, first, contacting an acid sphingomyelinase-deficient cell with a test compound, and exposing the cell to a stress stimulus. Next, an acid sphingomyelinase-deficient cell is exposed, in the absence of the test compound, to the stress stimulus. The levels of sphingomyelin and ceramide present in the exposed cells are compared, such that if the level of sphingomyelin in the cell exposed in presence of test compound is less than that of the cell exposed in the absence of the test compound, or the level of ceramide in the cell exposed in the presence of test compound is greater than that of the cell exposed in the absence of test compound, the test compound represents a compound which increases a cell's sensitivity to acid sphingomyelinase-related apoptosis.

The cells utilized in the above-described methods for identifying compounds which increase a cell's sensitivity to ASM-related apoptosis can be part of a genetically engineered nonhuman animal deficient for the acid sphingomyelinase gene, such that the animal is exposed to the stress stimulus, either in the presence or absence of test compound.

Sphingomyelin and ceramide assays, as well as methods for the production of acid sphingomyelinase deficient cells, cell lines and animals are described, below, in Section 5.3.

5.2. Screening Assays for Compounds that Decrease Sensitivity to ASM-Related Processes Methods for the identification of compounds which decrease a cell's sensitivity to ASM-related processes such as apoptosis are described in this Section. Such screens can identify targets in the apoptotic pathway in addition to ASM which, like ASM, are necessary for stress-induced apoptosis to occur. Further, such screens can identify compounds useful for minimizing the effects of stress-induced apoptosis, for example, radiation-induced apoptosis.

Such methods for identifying a compound which decreases a cell's sensitivity to acid sphingomyelinase-related apoptosis can include, for example, a method comprising, first, contacting a cell exhibiting acid sphingomyelinase activity with a test compound and exposing the cell to an apoptosis-inducing stress stimulus. Next, a cell which exhibits acid sphingomyelinase activity is exposed, in the absence of test compound, to the stress stimulus. The exposed cells are monitored for the presence of an apoptotic morphology, such that if the cell exposed in the presence of the test compound exhibits a less severe apoptotic morphology, than the cell exposed in the absence of the test compound, the test compound represents a compound which decreases a cell's sensitivity to acid sphingomyelinase-related apoptosis.

Such methods for identifying a compound which decreases a cell's sensitivity to acid sphingomyelinase-related apoptosis, can also include, for example, a method comprising, first, contacting a cell exhibiting acid sphingomyelinase activity with a test compound, and exposing the cell to stress stimulus. Next, a cell exhibiting acid sphingomyelinase activity is exposed; in the absence of test compound, to the stress stimulus. The levels of sphingomyelin and ceramide present in the exposed cells are compared such that if the level of sphingomyelin in the cell exposed in the presence of test compound is greater than that of the cell exposed in the absence of test compound, or the level of ceramide in the cell exposed in the presence of test compound, is less than that of the cell exposed in the absence of test compound, the test compound represents a compound which decreases a cell's sensitivity to acid sphingomyelinase-related apoptosis.

In the above-described methods for identifying compounds which decrease a cell's sensitivity to ASM-related apoptosis, the cells utilized can be transgenic cells comprising cells deficient in endogenous acid sphingomyelinase gene activity and containing a functional human acid sphingomyelinase transgene capable of expressing functional human acid sphingomyelinase. Further, such cells can be part of a genetically engineered nonhuman animal deficient in endogenous acid sphingomyelinase gene activity and containing integrated in its cells a functional human acid sphingomyelinase transgene capable of expressing functional human acid sphingomyelinase.

In the above-described methods for identifying compounds which decrease a cell's sensitivity to ASM-related apoptosis, the cells utilized can also be genetically engineered cells which exhibit a greater level of acid sphingomyelinase activity than non-genetically engineered cells of the same type.

Sphingomyelin and ceramide assays, and methods for the production of transgenic cells and animals comprising cells deficient in endogenous ASM gene activity and containing a functional human ASM transgene, and genetically engineered cells and animals which exhibit a greater level of acid sphingomyelinase activity than non-genetically engineered cells of the same type, are described, below, in Section 5.3.

5.3. Screening Assay Techniques

5.3.1. Apoptosis-Inducing Stimuli

The methods described in the Sections above can be used in identifying compounds which modulate a cell's sensitivity to ASM-related apoptosis. Among the apoptosis-inducing stimuli which can be tested are environmental stress agents, including but not limited to radiation, including ionizing radiation and/or chemotherapeutic agents.

Taking ionizing radiation as an example, cells and/or animals can be exposed to a radiation dosage range which will, preferably be between 0 and 30 Gy, administered according to standard techniques well known to those of skill in the art.

5.3.2. Apoptosis Assays

Cells can, in conjunction with the screening techniques described above, be assayed for apoptotic morphology using standard techniques well known to those of skill in the art. Among the characteristics of apoptotic morphology are cellular condensation, nuclear condensation, including chromatin condensation, and the apoptotic characteristic plasma membrane ruffling and bebbing referred to as "zeiosis" (Sanderson, C. J., 1982, in Mechanisms of Cell-Mediated Cytotoxicity, Clark, W. R. & Golstein, R., eds., Plenum Press, pp. 3–21; Godman, G. C. et al., 1075, J. Cell Biol. 64:644–667).

For example, morphologic changes characteristic of nuclear apoptosis can be assayed and quantified by stain the a DNA-specific fluorochrome such as bis-benzimide (Hoechst-33258; Sigma according to standard methods (Bose, et al., 1995, Cell 82:405–414).

In vivo, apoptosis can be assayed via, for example, DNA terminal transferase nick-end translation, or TUNEL assay, according to standard techniques (Fuks, Z. et al., 1995, Cancer J. 1:62–72).

5.3.3. ASM, Sphingomyelin and Cetamide Assays

Acid sphingomeylinase activity, sphingomyelin levels and ceramide levels can be measured via standard techniques well known to those of skill in the art. See, for example, Maruyama, E. N. & Arima, M., 1989, J. Neurochem. 52:611–618; Quintern, L. E. et al., 1991, Meth. Enzymol. 197:536–540; Wiegmann, K. et al., 1994, Cell 78:1005–1015, which are incorporated herein by reference in their entirety.

5.3.4. ASM Genes

Described in this Section are ASM-gene sequences which can be utilized in conjunction with the production of ASM-deficient and transgenic cells, cell lines and animals such as those which can be utilized with the screening techniques discussed, above.

The nucleotide sequence of the human ASM gene which can, for example, be utilized as the transgene in the production of transgenic cells and animals deficient in endogenous ASM activity, but capable of expressing a transgenic ASM gene, is well known. See, for example, pending U.S. patent application Ser. No. 07/695,472, now U.S. Pat. No. 5,773287, which is incorporated herein by reference in its entirety.

The nucleotide sequence of the mouse ASM gene is also known and can be utilized in the production of, for example, ASM-deficient cells, cell line and animal ("knock outs"), as well as in the production of ASM overexpressing cells, cell lines and genetically engineered animals. See, for example, Newrzella, D. & Stoffel, W., 1992, Hoppe-Seyler's Z. Bio. Chem. 373:1233–1238, which is incorporated herein by reference in its entirety.

In addition to the human and mouse ASM nucleotide sequences described above, ASM CDNA or gene sequences present in the same species and/or homologs of the ASM gene present in other species can be identified and readily isolated, without undue experimentation, by molecular biological techniques well known in the art. Such sequences can, for example, be utilized in the production of knock and/or transgenic cells, cell lines and/or animals of species other than human or mouse.

For example, cDNA libraries synthesized from mRNA, or genomic DNA libraries synthesized from genomic DNA, derived from the organism of interest can be screened by hybridization using either human or mouse ASM sequences, as described above, as hybridization or amplification probes.

Screening can be by filter hybridization, using duplicate filters. The labeled probe can contain at least 15–30 base pairs of an ASM nucleotide sequence. The hybridization washing conditions used should be of a lower stringency when the cDNA library is derived from an organism different from the type of organism from which the labeled sequence was derived.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, a labeled ASM nucleotide probe may be used to screen a genomic library derived from the organism of interest, again, using appropriately stringent conditions.

Further, an ASM gene homolog may be isolated from nucleic acid of the organism of interest by performing PCR using two degenerate oligonucleotide primer pools designed on the basis of ASM amino acid sequences encoded by the ASM sequences described above. The template for the reaction may be CDNA obtained by reverse transcription of mRNA prepared from, for example, human or non-human cell lines or tissue, known or suspected to express an ASM gene allele.

The PCR product may be subcloned and sequenced to ensure that the amplified sequences represent the sequences of an ASM gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the ASM gene). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

With respect to transgenes, human ASM transgenes are preferred. DNA containing the nucleotide coding sequence for an entire human ASM gene product, or any portion capable of encoding a functional ASM gene product may be used to produce ASM transgenic cells, cell lines and animals, such as, for example, those to be utilized as part of the screening methods described, above.

Due to the degeneracy of the genetic code, DNA sequences which encode the same or substantially same ASM gene product as that encoded by the human ASM nucleotide sequence described above can be utilized. The ASM nucleotide coding sequence used to produce the transgenic animals of the invention can be regulated by human ASM promoter regulatory nucleotide sequences. Alternatively, such sequences can be regulated by promoter sequences endogenous to the transgenes' host cells. Still further, any promoter which is capable of driving the expression of the ASM transgenic sequences in the transgenes' host cells can be utilized. Such regulatory sequences will be well known to those of skill in the art, and can include both constitutive and inducible regulatory sequences.

5.3.5. ASM Knockout and Transgenic Animals and Cells

Cells, cell lines and animals deficient for ASM activity can, as described above, be utilized as part of assays and screening techniques for the identification of compounds which modulate a cell's sensitivity to ASM-related apoptosis. The term "ASM-deficient", as used herein, refers to cells, cell lines and/or animals which exhibit a lower level of functional ASM activity than corresponding cells, or cell lines or animals whose cells, contain two normal, wild type copies of the ASM gene. Preferably, "ASM-deficient" refers to an absence of detectable functional ASM activity.

A representative ASM-deficient, or "knockout" animal is a mouse ASM-deficient animal. Such animals are well known to those of skill in the art. See, for example, Horinouchi, K. et al., 1995, Nature Genetics 10:288–293; and Otterbach, B. & Stoffel, W., 1995, Cell 81:1053–1061, both of which are incorporated herein by reference in their entirety. Techniques for generating additional ASM knockout cells, cell lines and animals are described below.

Cells and cell lines deficient in ASM activity can be derived from ASM knockout animals, utilizing standard techniques well known to those of skill in the art. Such animals may be used to derive a cell line which may be used as an assay substrate in culture. While primary cultures may be utilized, the generation of continuous cell lines is preferred. For examples of techniques which may be used to derive a continuous cell line from the transgenic animals, see Small et al., 1985, Mol. Cell Biol. 5:642–648. Such techniques for generating cells and cell lines can also be utilized in the context of the transgenic and genetically engineered animals described below.

Further, ASM deficient cells can include cells taken from and cell lines derived from patient exhibiting Niemann-Pick disease, a disorder caused by an ASM deficiency. Such cells can include, for example, cells containing ASM mutations such as those described in U.S. patent application Ser. No. 08/250,740, now U.S. Pat. No. 5,686,240, which is incorporated herein by reference in its entirety. Representative ASM-deficient cell include MS1271 cells. MS1271 cells contain one allele of the ΔR608 mutation and one allele of the R496L mutation (Levran et al., 1991, Proc. Natl. Acad. Sci. USA 88:37848–3752). Additional ASM-deficient cells and cell lines can be generated using well known recombinant DNA techniques such as, for example, site-directed mutagenesis, to introduce mutations into ASM gene sequences which will disrupt ASM activity.

Cells, cell lines and animals deficient for endogenous ASM activity and, further, containing an ASM transgene, preferably a human ASM transgene, capable of being expressed in the transgene, can also, as described above, be utilized as part of assays and screening techniques for the identification of compounds which modulate a cell's sensitivity to ASM-related apoptosis. Techniques for generating such transgenic cells, cell lines and animals are described below.

Further, genetically engineered cells, cell lines and animals which exhibit a greater level of ASM activity than non-genetically engineered cells of the same type can also, as described above, be utilized as part of assays and screening techniques for the identification of compounds which modulate a cell's sensitivity to ASM-related apoptosis. Techniques for generating such genetically engineered cells, cell lines and animals are described below. Utilizing techniques such as those described above, for example, multiple copies of ASM transgenic or endogenous constructs may be arranged within a vector may be stably introduced into the transgenic founder animals to yield animals exhibiting overexpression of ASM.

ASM transgenic, ASM-deficient and ASM-overexpressing animals can be generated using the ASM nucleotide sequences discussed, above, in Section 5.3.4. Such animals can be any species, including but not limited to mice, rats, rabbits, guinea pigs, pigs, micro-pigs, and non-human primates, e.g., baboons, squirrel monkeys and chimpanzees.

Any technique known in the art may be used to introduce a transgene (either a functional endogenous or heterologous transgene or, alternatively, an inactivating gene sequence) into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety).

As listed above, standard embryonal stem cell (ES) techniques can, for example, be utilized for generation of ASM knockout, ASM-deficient and ASM-overexpressing animals. ES cells can be obtained from preimplantation embryos cultured in vitro (See, e.g., Evans, M. J. et al., 1981, Nature 292:154–156; Bradley, .O. et al., 1984, Nature 309:255–258; Gossler et al., 1986, Proc. Natl. Acad. Sci. USA 83:9065–9069; Robertson et al., 1986, Nature 322:445–448; Wood, S. A. et al., 1993, Proc. Natl. Acad. Sci. USA 90:4582–4584.)

Transgenes, which can include, for example, additional copies of endogenous or heterologous ASM gene sequences (for, e.g., the production of overexpressing ASM animals) and can, additionally contain transgenic ASM gene sequences to be utilized as part of the production, e.g., of ASM transgenic animals deficient for endogenous ASM activity but capable of expressing an ASM transgene can efficiently be introduced into ES cells by standard techniques such as DNA transfection or retroviral-mediated transduction. The resultant transformed ES cells can thereafter be combined with blastocysts from a non-human animal. The introduced ES cells thereafter colonize the embryo and contribute to the germ line of a resulting chimeric animal (Jaenisch, R., 1988, Science 240:1468–1474).

To accomplish ASM gene disruptions, either in the production of ASM knockout animals or as part of the production of ASM transgenic animals deficient for endogenous ASM activity, but containing a functional ASM transgene, the technique of site-directed inactivation via gene targeting (Thomas, K. R. and Capecchi, M. R., 1987, Cell 51:503–512) and review in Frohman et al., 1989, Cell 56:145–147; Cappecchi, 1989, Trends in Genet. 5:70–76; Barribault et al., 1989, Mol. Biol. Med. 6:481–492; Wagner, 1990; EMBO J. 9:3025–3032; and Bradley et al., 1992, Bio/Technology.

Further, standard techniques such as, for example, homologous recombination, coupled with the ASM sequences described, above, in Section 5.3.4, can be utilized to inactivate or alter any ASM genetic region desired. A number of strategies can be utilized to detect or select rate homologous recombinants. For example, PCR can be used to screen pools of transformant cells for homologous insertion, followed by screening of individual clones (Kim et al., 1988, Nucl. Acids Res. 16:8887–8903; Kim et al., 1991, Gene 103:227–233). Alternatively, a positive genetic selection approach can be taken in which a marker gene is constructed which will only be active if homologous insertion occurs, allowing these recombinants to be selected directly (Sedivy et al., 1989, Proc. Natl. Acad. Sci. USA 86:227–231). Additionally, the positive-negative approach (PNS) method can be utilized (Mansour et al., 1988, Nature 336:348–352; Capecchi, 1989, Science 244:1288–1292; Capecchi, 1989, Trends in Genet. 5:70–76). Utilizing the PNS method, nonhomologous recombinants are selected against by using the Herpes Simplex virus thymidine kinase (HSV-TK) gene and selecting against its nonhomologous insertion with herpes drugs such as gancyclovir or FIAU. By such counter-selection, the number of homologous recombinants in the surviving transformants is increased.

ES cells generated via techniques such as these, when introduced into the germline of a nonhuman animal make possible the generation of non-mosaic, i.e., non-chimeric progeny. Such progeny will be referred to herein as founder animals. Once the founder animals are produced, they may be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic mice to produce mice homozygous for a given integration site in order to both augment expression and eliminate the need for screening of animals by DNA analysis; crossing of separate homozygous lines to produce compound heterozygous or homozygous lines; breeding animals to different inbred genetic backgrounds so as to examine effects of modifying alleles on expression of the transgene and the neuropathological effects of expression.

6. EXAMPLE: ASM IS REQUIRED FOR RADIATION-INDUCED APOPTOSIS

The present studies address the role of ceramide generation via acid sphingomyelinase in induction of apoptosis using two separate genetic models. Lymphoblast cell lines from Niemann-Pick disease (NPD) patients demonstrated a defect in radiation-induced apoptosis which was reversible upon restoration of acid sphingomyelinase activity. Defects in radiation-induced apoptosis were also observed in tissues of acid sphingomyelinase knock-out mice, which contain physiologic levels of neutral sphingomyelinase activity

6.6 MATERIALS AND METHODS

Cell Culture

EBV-transformed lymphoblasts were established by standard techniques (Anderson, M. A. & Gusella, J. F., 1984, In Vitro 20:856–858.) from two NPD patients, designated MS1271 and MS1418. MS1271 is an Ashkenazi Jewish Type B patient who is currently 11 years of age and neurologically intact. He carries one allele of the Type B mutation, AR608 (Levran, O., et al., 1991, J. Clin. Invest. 88:806–810), and another of the mutation R496L (Levran, O. et al., 1991, Proc. Natl. Acad. Sci. USA 88:3748–3752). Cultured skin fibroblasts from this patient have less than 3% of normal acid sphingomyelinase activity. MS1418 was derived from a 3 year old American boy of German ancestry who presented with massive hepatosplenomegaly[ ]and severe retardation. He was treated for recurrent pneumonia and subsequently died when he was five years of age. Cultured cells from patient MS1418 have <1% of normal acid sphingomyelinase activity. EBV-transformed lymphoblasts derived from NPD patients or unaffected controls were maintained in a mixture of RPMI and DMEM media (4:1; v/v) containing 18% fetal calf serum (FBS) (Gibco BRL). Cells were grown at 37° C. in a 5% $CO_2$ atmosphere. Cell number and viability were assessed by Trypan Blue exclusion analysis. Amphotropic packaging cell lines which secrete acid sphingomyelinase-containing retrovirus (Yeyati, P. L. et al., 1995, Human Gene Therapy 6:975–983), were maintained in DMEM media with 10% FBS.

For gene transfer, retrovirus packaging cells were plated in 100 mm Transwell dishes (Costar), above the 0.45 mm membrane insert, at $10–40 \times 10^6$ cells per dish, and grown overnight. An equal number of lymphoblasts were layered beneath the Transwell insert on the following day. After 48 hours of co-culture, infected lymphoblasts were removed from the dish and grown in fresh media. Expression of acid sphingomyelinase activity was maximal at 24–48 hours postinfection. Experiments were routinely performed at 24 hours post-infection.

Mice and Irradiation

Four to six week old male C3H/HeJ and C57BL/6 (p53+/+) mice were purchased from the Jackson Laboratories (Bar Harbor, Maine), and 129/SV and p53 knock-out mice were purchased from Taconic Labs (Germantown, N.Y.). Acid sphingomyelinase knock-out mice were constructed as described (Horinouchi, K. et al, 1995, Nature Genet. 10:288–293). Briefly, embryonic stem (ES) cells derived from 129/SV mice were transfected with an acid sphingomyelinase replacement vector containing a neomycin expression cassette inserted into exon 2 of the acid sphingomyelinase gene. ES cell colonies containing the properly targeted acid sphingomyelinase sequences were obtained and then microinjected into blastocysts of C57BL/6 mice. The resulting chimeric mice were used to generate the acid sphingomyelinase knock-out mouse colony. The homozygous acid sphingomyelinase knock-out phenotype is inherited as an autosomal recessive trait. For experiments, animals received whole body irradiation, delivered using a Cs-137 Irradiator (Shepherd Mark-I, Model 68, SN643), at a dose rate of 270 cGy/min.

Lipid Studies

On the day of an experiment, cells were resuspended into media without serum ($2 \times 10^6$ cells/0.3 ml) and irradiated. Doses are indicated in each figure. Ceramide was quantified by the diacylglycerol kinase assay as described (Dressler, & Kolesnick, R. N., 1990, J. Biol. Chem. 256:14917–14921). Briefly, after irradiation, cells were incubated at 37° C. for various lengths of time and extracted with 1 ml chloroform:methanol:1 N HCl (100:100:1, v/v/v). Lipids in the organic phase were dried under N2 and subjected to mild alkaline hydrolysis (0.1 N methanolic KOH for 1 h at 37° C.) to remove glycerophospholipids. Samples were reextracted and lipids in the organic phase extract were quantified via the diacylglycerol kinase reaction.

For measurement of sphingomyelin levels, cells were labeled to isotopic equilibrium with [3H]choline (1 mCi/ml; Dupont NEN, specific activity 79.2 Ci/mmol) for at least 3 cell doublings (Dressler, K. A. et al., 1992, Science 255:1715–1718.). Lipids were extracted as above and sphingomyelin was resolved by thin layer chromatography, using chloroform:methanol:acetic acid:water (50:30:8:4) as solvent, identified by iodine vapor staining, and quantified by liquid scintillation counting. Baseline sphingomyelin mass was verified by lipid phosphorous assay (Chen, J. P. S. et al., 1956, Anal. Chem. 28:1756–1758.).

Tissue ceramide content was determined by a modification of the method used for amino acid analyses (Merrill, J.-A. H. et al., 1988, Anal. Biochem. 171:373–381.). After irradiation, animals were sacrificed by cervical dislocation and tissues were weighed and homogenized in 8 vol (w/v) of ice-cold PBS. Homogenate (0.4 ml) was transferred to 16×100 mm glass tubes and lipids were extracted with 2 ml of chloroform:methanol (2:1, v/v). Ceramide in the organic phase was measured after deacylation to sphingoid base and derivitization with o-phthaldehyde (OPA) as described by Merrill et al., 1988. Briefly, aliquots of the organic phase (250 ml) were dried under N2, resuspended in 0.5 ml of 1 N KOH in methanol and incubated for 1 hour at 100° C. to deacylate ceramide to free sphingoid bases (Van Veldhoven, P. et al., 1989, Anal. Biochem 183:177–189). Lipids were then dissolved in 50 ml methanol and mixed with 50 ml of o-phthaldehyde reagent, which was prepared fresh daily by mixing 99 ml of 3% (w/v) boric acid in water (pH adjusted to 10.5 with KOH) and 1 ml of ethanol containing 50 mg of OPA (Sigma) and 50 ml of 2-mercaptoethanol. After incubation for 5 min at room temperature, 500 ml of methanol:5 mM potassium phosphate (pH 7.0) (90:10; v/v) was added, and the samples were clarified by brief centrifugation. Aliquots (20 ml) were quantified by reverse phase high performance liquid chromatography (HPLC) using a Nova Pak C18 column (60 Å, 4 μm, 3.9 mm×150 mm; Waters). Fluorescent lipids were eluted isocratically with methanol:5 mM potassium phosphate, pH 7.0 (90:10; v/v) at a flow rate of 0.6 ml/min and detected by spectrofluorometer (excitation wavelength 340 nm, emission wavelength 455 nm). Ceramide levels were determined by comparison to a concomitantly run standard curve of known amounts of ceramide (Type III: from bovine brain sphingomyelin; Sigma). The levels of ceramide obtained by this procedure were similar to those obtained by the diacylglycerol kinase assay.

Acid Sphingomyelinase Assay

Cells ($1-2\times10^7$) were pelleted (500 x g, 5 min, 4° C.), washed twice with ice-cold PBS and resuspended ($1\times10^6$ cells/0.3 ml) into homogenization buffer (0.2% Triton X-100). Cells were disrupted with a Tenbroeck tissue homogenizer (Bellco glass) and nuclei and debris were pelleted by centrifugation at 800 x g for 5 min.

Acid sphingomyelinase activity was measured as described (Maruyama, E. N., & Arima, M., 1989, J. Neurochem. 52:611– 618). Incubations contained 30 mg of post-nuclear supernatant and 15 ml of sphingomyelin substrate (9 nmol sphingomyelin mixed with 0.9 ml of [$^{14}$C] sphingomyelin, specific activity 56 mCi/mmol; Amersham) in acid sphingomyelinase assay buffer (250 mM Na acetate pH 5.2, 1 mM EDTA, 0.1% Triton X-100). After 2 hours at 37° C., 14C-phosphocholine was extracted with 200 ml of chloroform:methanol (1:1 v/v) and 90 ml of H2O. Aliquots of the aqueous phase extract were quantified by liquid scintillation counting. Acid sphingomyelinase activity is expressed as nmols sphingomyelin hydrolyzed/mg protein/hr.

Apoptosis

Morphological changes of nuclear apoptosis were visualized by staining with the DNA-binding fluorochrome bisbenzimide (Hoechst-33258, Sigma) as described (Bose, R., et al., 1995, Cell 82:405–414). Briefly, $0.5-2.0\times10^6$ cells were pelleted, washed once with PBS, and fixed in 500 ml of 3% paraformaldehyde in PBS. Thereafter, cells were resuspended into 30 ml paraformaldehyde/PBS containing 16 mg/ml bisbenzimide. Aliquots were placed on glass slides, and evaluated by fluorescence microscopy (Olympus BH-2 fluorescence microscope with a BH2-DMU2UV Dich Mirror Cube filter). A minimum of 500 cells were scored for the incidence of apoptotic chromatin changes (condensation of chromatin, its compaction along the periphery of the nucleus, and segmentation of the nucleus into greater than 3 fragments).

Apoptosis in vivo was assessed by the DNA terminal transferase nick-end translation method or TUNEL assay, as described (Fuks, Z., et al., 1994, Cancer Res. 54:2582–2590). Briefly, tissue specimens were fixed overnight in 4% buffered formaldehyde and embedded in paraffin blocks. Tissue sections (5 mm thick), adherent to polylysine-treated slides, were deparaffinized by heating at 90° C. for 10 minutes and then at 60° C. for 5 minutes. Tissue-mounted slides were first washed with 90% and then 80% ethanol (3 minutes each) and rehydrated. The slides were incubated in 10 mM Tris-HCl, pH 8 for 5 min, digested with 0.1% pepsin, rinsed in distilled water and treated with 3% H2O2 in PBS for 5 min at 22° C. to inactivate endogenous peroxidase. After 3 washes in PBS, the slides were incubated for 15 min at 22° C. in buffer (140 mM Na-cacodylate, pH 7.2,30 mM Trizma base, 1 mM CoCl2) and then for 30 minutes at 37° C. in reaction mixture (0.2 U/ml terminal deoxynucleotidyl transferase, 2 nM biotin-11-dUTP, 100 mM Na-cacodylate, pH 7.0, 0.1 mM DTT, 0.05 mg/ml BSA and 2.5 mM CoCl2). The reaction was stopped by transferring the slices to a bath of 300 mM NaCl, 30 mM Na citrate for 15 min at 22° C. The slides were washed in PBS, blocked with 2% human serum albumin in PBS for 10 min, re-washed and incubated with avidin-biotin peroxidase. After 30 minutes at 22° C., cells were stained with the chromogen 3,'diamonobenzidine tetrachloride and counterstained with hematoxylin. Nuclei of apoptotic cells appear brown and granular, while normal nuclei stain blue.

Statistical Analysis

Statistical analyses were performed by Student's test and Chi Square test.

6.2 RESULTS 6.2.1. Radiation Induces Apoptosis in Normal Lymphoblast but not in Lymphoblasts from NPD Patients FIG. 1A shows that exposure of EBV-transformed normal human lymphoblasts to a radiation dose of 20 Gy resulted in time-dependent apoptosis as defined by morphologic changes of chromatin condensation and compaction, and nuclear segmentation. Apoptosis was detected by 8 hours and was maximal by 24 hours. As little as 1 Gy was effective and a peak effect was achieved with 20 Gy (FIG. 1B). In contrast, the EBV-transformed NPD lymphoblast lines MS1418 (FIGS. 1A,B) and MS1271 did not demonstrate a significant apoptotic response. The differences in the apoptotic response could not be attributed to altered cell proliferation, because the growth rates of NPD and normal lymphoblasts did not differ appreciably.

6.2.2. Radiation Induces Ceramide Generation in Normal Lymphoblasts but Not in Lymphoblasts From NPD Patients To determine whether these differences correlated with differences in ceramide generation, normal and NPD lymphoblasts were exposed to ionizing radiation and sphingomyelin hydrolysis to ceramide was measured. Lymphoblasts from two normal individuals displayed acid sphingomyelinase activity of 6.0+0.2 nmol sphingomyelin hydrolyzed/mg protein/hr (mean+range). The NPD lines, MS1418 and MS1271, expressed only 2–3% residual acid sphingomyelinase activity of 0.19 and 0.13 nmol sphingomyelin hydrolyzed/mg protein/hr, respectively, consistent with previously published data (Suchi, M. et al., 1992, Proc. Natl.

Acad. Sci. 89:3227–3231). FIG. 1C shows that a dose of 20 Gy induced a rapid reduction in sphingomyelin content in normal lymphoblasts from a baseline level of 440 pmol/106 cells. This effect was detected by 2 min and persisted for 30 minutes ($p<0.001$ vs. basal level). The reduction in sphingomyelin content was accompanied by a near quantitative increase in ceramide above a basal level of 180 pmol/106 vells (FIG. 1D). Ceramide elevation was detected by 1–2 min and was maximal at 15 min ($p<0.001$ vs. basal level). Consistent with the deficiency in acid sphingomyelinase activity, MS1271 lymphoblasts had elevated basal levels of sphingomyelin of 565 pmol/106 cells. These cells did not respond to 20 Gy radiation at any time between 0–30 min with a decrease in sphingomyelin (FIG. 1C) or an increase in ceramide content (FIG. 1D). Similar results were obtained with the NPD line MS1418, which exhibits a higher baseline sphingomyelin content of 1,110 pmol/106 cells. It should be noted that the lack of response was specific for deficiency of acid sphingomyelinase since these NPD lymphoblasts contain a normal level of neutral sphingomyelinase activity of 2.2 nmol sphingomyelin hydrolyzed/mg protein/hr.

6.2.3. Retroviral Transfer of Acid Sphingomyelinase CDNA Restores Radiation-Induced Ceraminde Generation and Apoptosis to NPD Lymphoblasts To demonstrate a role for acid sphingomyelinase in induction of apoptosis by ionizing radiation, acid sphingomyelinase activity was restored to the NPD lymphoblasts by retroviral transfer. Retroviral transduction of the human acid sphingomyelinase cDNA into the NPD lymphoblast lines increased acid sphingomyelinase activity 17-fold in MS1418 cells to 3.24 nmol sphingomyelin hydrolyzed/mg protein/hr and 8-fold in MS1271 cells to 1.03 nmol sphingomyelin hydrolyzed/mg protein/hr. Routinely, expression was greater in line MS1418 than in MS1271. Introduction of the acid sphingomyelinase cDNA restored radiation-induced ceramide generation to MS1271 (FIG. 2A) and MS1418 cells, and apoptosis (FIG. 2B,C). In contrast, retroviral transduction of an irrelevant cDNA for the enzyme arylsulfatase did not restore radiation-induced ceramide generation or apoptosis to MS1271 or MS1418 cells.

6.2.4. Acid Sphingomyelinase Knock-Out Mice have a Defect in Radiation-Induced Apoptosis In previous studies, it was reported that ionizing radiation induced marked apoptotic changes in the lungs of C3H/HeJ mice in vivo, as measured by the DNA-terminal transferase nick-end translation method (TUNEL) assay (Fuks, z. et al., 1994, Cancer Res. 54:2582–2590). The walls of pulmonary alveoli consist of an extensive network of capillaries, which allow for efficient gas exchange, and type I and II pneumocytes for support. The prior investigations showed that the apoptotic response in the irradiated lung was largely confined to microvascular endothelial cells. This effect was detected by 6 hours after irradiation and was maximal by 10 hours. Thereafter, apoptotic cells were phagocytized by alveolar macrophages and could no longer be detected by 24 hours.

To determine whether ceramide might play a role in radiation-induced apoptosis in this mouse lung model, wild type C3H/HeJ mice were exposed to 10 Gy whole body radiation, and ceramide content was measured in extracts of lung tissue. Ceramide generation above a basal level of 280 nmol/g lung tissue was detected as early as 5 minutes after irradiation and was maximal by 30 minutes. Thus ceramide generation preceded the onset of apoptosis. The effect of radiation on ceramide generation was dose-dependent. As little as 7.5 Gy was effective and a maximal effect to 232% of control was demonstrated after 20 Gy at 30 min. This dose range is consistent with that previously shown to induce apoptosis in lungs of C3H/HeJ mice (Fuks, Z., et al., 1994, Cancer Res. 54:2582–2590). It is believed that this is the first demonstration of stress-induced ceramide generation in vivo.

To analyze the role of acid sphingomyelinase in radiation-induced ceramide generation and apoptosis in vivo, an acid sphingomyelinase-deficient mouse model was employed. Acid sphingomyelinase knock-out mice were generated by targeted disruption of the acid sphingomyelinase gene of 129/SV mice within exon 2 (Horinouchi, K. et al., 1995, Nature Genet. 10:288–293.). Homozygous acid sphingomyelinase knock-out mice appear normal at birth and develop routinely until about four months of age, when they begin to show signs of neurologic disease including ataxia, tremors and loss of appetite (Otterbach, B., & Stoffel, W., 1995, Cell 81:1053–61.; Horinouchi, K. et al., 1995, Nature Genet. 10:288–293.). Affected animals have no detectable acid sphingomyelinase activity and accumulate sphingomyelin and cholesterol in various tissues as their disease progresses (Horinouchi, K. et al., 1995, Nature Genet. 10:288–293.). Acid sphingomyelinase knock-out mice were analyzed within 3 weeks of weaning, a time at which no disease manifestations are detected.

Figure 3B:
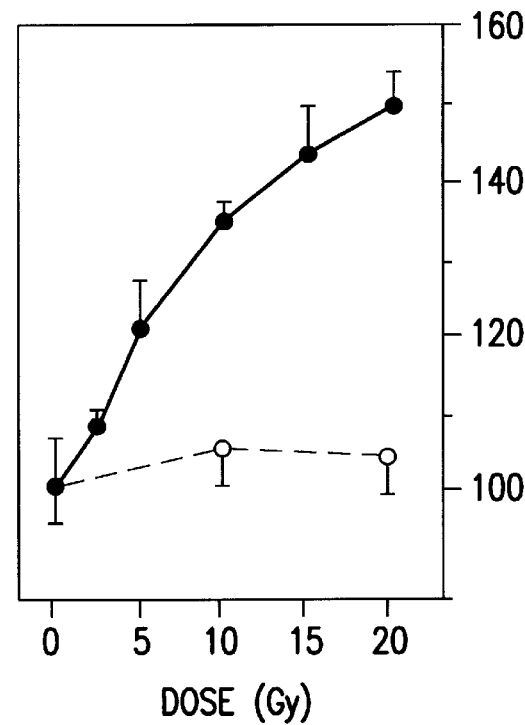

Similar to C3H/HeJ mice, radiation induced time- and dose-dependent ceramide generation above a basal level of 225 nmol/g tissue in the lungs of the wild type 129/SV mice (FIG. 3). However, radiation did not increase ceramide content in the lungs of the acid sphingomyelinase knock-out mice. Exposure to 20 Gy induced extensive apoptosis in the lungs of wild type 129/SV mice after 10 hours (FIG. 4; left upper panel). Higher magnification of the these tissue specimens demonstrated that apoptosis occurred primarily in the endothelium (FIG. 4; left lower panel). In contrast, acid sphingomyelinase-deficient mice did not exhibit significant pulmonary apoptosis in response to 20 Gy (FIG. 4C; right panel). Increasing the radiation dose up to 30 Gy failed to generate an apoptotic response in the lungs of the acid sphingomyelinase-deficient mice.

The effect of radiation to induce apoptosis was also evaluated in thymic and splenic tissue from 129/SV and C3H/HeJ mice. Both strains yielded identical results. Apoptosis occurred more rapidly in thymic than lung tissue, and the response was biphasic. A rapid phase, detected by 1 hour with 7.5 Gy, peaked at 3 hours, and was followed by a slower response (FIG. 5A). As little as 2 Gy was effective and a maximal effect was achieved with 10 Gy. As compared to the lung, the acid sphingomyelinase knock-out mice demonstrated a less comprehensive defect in radiation-induced apoptosis in thymic tissue. Unirradiated thymic tissue from normal and knock-out animals manifested a baseline 4–5% incidence of apoptosis. FIG. 6 shows that a dose of 5 Gy induced substantial apoptosis in the thymic cortex of 129/SV mice at 2.5 hours after irradiation. Many of the apoptotic cells formed clusters of 5–8 cells surrounded by normal appearing cells. In contrast, minimal apoptosis was detected in the thymic cortex of the acid sphingomyelinase knock-out mice. When 2000 129/SV thymic cells were counted in four high-power fields (FIG. 5B), a total of 652 (33%) showed apoptotic changes. In contrast, only 346 (17%) of 2000 cells in the thymic cortex of the acid sphingomyelinase knock-out mouse were apoptotic ($p<0.0001$). Statistically significant differences in thymic apoptosis were also observed between 129/SV and knock-out mice at 4 Gy and 7.5 Gy (FIG. 6C). After 4 hours, there was a rapid increase in the incidence of apoptosis in both strains. A diffuse pattern gradually developed throughout the thymic cortex and detectable differences diminished, perhaps due to overcrowding by the late responding apoptotic cells. Differences were no longer detected by 10 hours. Qualitatively similar results were observed in the spleen (FIG. 5B).

6.2.5. Comparison of p53 and Acid Syhingomyelinase Knock-Out Mice

Because of the variation in tissue responses of the acid sphingomyelinase knock-out mice, p53 knockout mice, also known to be defective in radiation-induced apoptosis, were studied. FIG. 7 shows apoptotic responses to 20 Gy in wild type C57Bl/6 mice and the p53 knock-out mice derived from this strain. Both the cortex (left upper panel) and medulla of the wild type thymus demonstrated diffuse apoptosis at 10 hours. In contrast, only 13% of the thymic cells of the p53 knock-out mice expressed apoptotic changes (right upper panel), appearing mostly in clusters of 5–8 cells. Increasing the radiation dose to 30 Gy failed to increase the apoptotic response in the thymus of the p53-deficient mice. These in vivo studies agree with previous ex vivo studies, which reported a 10–20% incidence of radiation-induced apoptosis in thymocytes derived from p53 knock-out mice (Strasser, A. et al., 1994, Cell 79:329–339; Lowe, S. W., et al., 1993. p53-Dependent apoptosis modulates the cytotoxicity of anticancer agents. Cell 74:957–967.).

In contrast to the thymus, lungs of p53-deficient mice (lower right panel) exhibited a normal apoptotic response at 10 hours after exposure to 20 Gy. The effect appeared identical to that observed in wild-type C57Bl/6 mice (lower left panel), and in 129/SV (FIG. 4) and C3H/HeJ mice (Fuks, Z., et al., 1994, Cancer Res. 54:2582–2590). It should again be noted that the lungs of acid sphingomyelinase-deficient mice did not undergo apoptosis in response to radiation (FIG. 4).

To explore the sensitivity of other p53-deficient tissues to radiation-induced apoptosis, knock-out mice were exposed to whole-body radiation (20 Gy). Apoptotic responses were observed at 10 hours in the pleura, endocardium, pericardium, and the germinal centers of the spleen. Apoptotic responses were not observed in liver, kidney, brain, skin, the myocardium and striated muscle. This pattern of tissue response was identical to that observed in C57Bl/6, 129/SV and C3H/HeJ mice when exposed to a similar radiation dose. However, the radiation response in acid sphingomyelinase knock-out mice differed. These mice did not develop apoptosis in endocardium, pericardium or pleura.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for identifying a compound which increases a cell's sensitivity to acid sphingomyelinase-related apoptosis, comprising:
   (a) contacting an acid sphingomyelinase-deficient cell with a test compound;
   (b) exposing the cell to a radiation stress stimulus for a time sufficient to induce apoptosis in a cell exhibiting normal acid sphingomyelinase activity;
   (c) exposing an acid sphingomyelinase-deficient cell, in the absence of the test compound, to the radiation stress stimulus for a time sufficient to induce apoptosis in a cell exhibiting normal acid sphingomyelinase activity; and
   (d) monitoring the exposed cells of steps (b) and (c) for the presence of an apoptotic morphology,
   such that if the cell from step (b) exhibits a more severe apoptotic morphology, than that of the cell from step (c) the test compound represents a compound which increases a cell's sensitivity to acid sphingomyelinase-related apoptosis.

2. A method for identifying a compound which increases a cell's sensitivity to acid sphingomyelinase-related apoptosis, comprising:
   (a) exposing acid sphingomyelinase-deficient cells, wherein the cells are part of cell lines or a genetically engineered nonhuman animal deficient for the acid sphingomyelinase gene, in the presence or the absence of a test compound, to a radiation stress stimulus for a time sufficient to induce apoptosis in a cell exhibiting normal acid sphingomyelinase activity; and
   (b) monitoring the exposed cells of step (a) for the presence of an apoptotic morphology, such that if the cells treated with the test compound exhibit a more severe apoptotic morphology than that of the cells not treated with the test compound, the test compound represents a compound which increases a cell's sensitivity to acid sphingomyelinase-related apoptosis.

3. The method of claims 1 or 2 wherein the apoptotic morphology comprises cellular condensation, nuclear condensation or zeiosis.

4. A method for identifying a compound which increases a cell's sensitivity to acid sphingomyelinase-related apoptosis, comprising:
   (a) contacting an acid sphingomyelinase-deficient cell with a test compound;
   (b) exposing the cell to a radiation stress stimulus;
   (c) exposing an acid sphingomyelinase-deficient cell, in the absence of the test compound, to the radiation stress stimulus; and
   (d) comparing the levels of sphingomyelin and ceramide present in the exposed cell of step (b) to the levels present in the exposed cell of step (c),
   such that if the level of sphingomyelin in the cell of step (b) is less than that of the cell of step (c)., or the level of ceramide in the cell of step (b) is greater than that of the cell in step (c), the test compound represents-a compound which increases a: cell-'s-sensitivity to acid sphingomyelinase-related apoptosis.

5. A method for identifying a compound which decreases a cell's sensitivity to acid sphingomyelinase-related apoptosis, comprising:
   (a) contacting a cell exhibiting acid sphingomyelinase activity with a test compound;
   (b) exposing the cell to a radiation stress stimulus;
   (c) exposing a cell exhibiting acid sphingomyelinase activity to the radiation stress stimulus, in the absence of the test compound; and
   (d) comparing the levels of sphingomyelin and ceramide present in the exposed cell of step (b) to the levels present in the exposed cell of step (c), such that if the level of sphingomyelin in the cell of step (b) is greater than that of the cell of step (c), or the level of ceramide in the cell of step (b) is less than that of the cell in step (c), the test compound represents a compound which decreases a cell's sensitivity to acid sphingomyelinase-related apoptosis.

6. A method for identifying a compound which increases a cell's sensitivity to acid sphingomyelinase-related apoptosis, comprising:

(a) exposing acid sphingomyelinase-deficient cells, wherein the cells are part of cell lines or a genetically engineered nonhuman animal deficient for the acid sphingomyelinase gene, in the presence or the absence of a test compound, to a radiation stress stimulus for a time sufficient to induce apoptosis in a cell exhibiting normal acid sphingomyelinase activity; and (b) comparing the levels of sphingomyelin and ceramide present in cells treated with test compound to cells untreated with the test compound, such that if the level of sphingomyelin in the cells treated with the test compound is less than that of cells not treated with the test compound, or the level of ceramide in cells treated with the test compound is greater than in cells not treated with the test compound, the test compound represents a compound which increases a cell's sensitivity to acid sphingomyelinase-related apoptosis.

7. A method for identifying a compound which decreases a cell's sensitivity to acid sphingomyelinase-related apoptosis, comprising:

(a) exposing transgenic cells, comprised of cells deficient in endogenous acid sphingomyelinase gene activity that contain a functional human acid sphingomyelinase gene capable of expressing functional human acid sphingomyelinase, to a radiation stress stimulus in the presence or absence of a test compound; and (b) comparing the levels of sphingomyelin and ceramide present in cells treated with test compound to cells not treated with the test compound, such that if the level of sphingomyelin in cells treated with the test compound is greater than in cells not treated with the test compound, or the level of ceramide in cells treated with the test compound is less than that of cells not treated with the test compound, the test compound represents a compound which decreases a cell's sensitivity to acid sphingomyelinase-related apoptosis.

8. The method of claim 7 wherein the cell is part of a genetically engineered nonhuman animal deficient in endogenous acid sphingomyelinase gene activity and containing integrated in its cells a functional human acid sphingomyelinase transgene capable of expressing functional human acid sphingomyelinase.

9. A method for identifying a compound which decreases a cell's sensitivity to acid sphingomyelinase-related apoptosis, comprising, (a) exposing cells, wherein the cells are genetically engineered cells that exhibit a greater level of acid sphingomyelinase activity than non-genetically engineered cells of the same type, to a radiation stress stimulus in the presence or absence of a test compound; and (b) comparing the levels of sphingomyelin and ceramide present in cells treated with the test compound to cells not treated with the test compound, such that if the level of sphingomyelin in cells treated with the test compound is greater than in cells not treated with the test compound, or the level of ceramide in cells treated with the test compound is less than that of cells not treated with test compound, the test compound represents a compound which decreases a cell's sensitivity to acid sphingomyelinase-related apoptosis.

* * * * *

UNITED STATES PATENT AND TRADEMARK OFFICE
CERTIFICATE OF CORRECTION

PATENT NO. : 6,274,309 B1
DATED : August 14, 2001
INVENTOR(S) : Kolesnick et al.

It is certified that error appears in the above-identified patent and that said Letters Patent is hereby corrected as shown below:

<u>Title page,</u>
Item [56], OTHER PUBLICATIONS, delete all references followed by an asterisk.

<u>Column 6,</u>
Line 25, please delete "Compounds identified very screens" and substitute therefor -- Compounds identified by screens --.
Line 33, please delete "compounds which act increase" and substitute therefor -- compounds which act to increase --.
Line 47, please delete "observed in 'stress-exposed" and substitute therefor -- observed in stress-exposed --.

<u>Column 8,</u>
Lines 54-55, please delete "quantified by stain the a DNA-specific" and substitute therefor -- quantified by staining with a DNA-specific --

<u>Column 9,</u>
Line 31, please delete "ASM CDNA or gene sequences" and substitute therefor -- ASM cDNA or gene sequences --.
Line 36, please delete "utilized in the production of knock and/or transgenic cells" and substitute therefor -- utilized in the production of knock-out and/or transgenic cells --.

<u>Column 10,</u>
Line 2, please delete "may be CDNA obtained" and substitute therefor -- may be cDNA obtained --.

<u>Column 11,</u>
Line 19, please delete "cell lines derived from patient exhibiting" and substitute therefor -- cell lines derived from a patient exhibiting --.

<u>Column 13,</u>
Line 38, please delete "levels of neutral sphingomyelinase activity" and substitute therefor -- levels of neutral sphingomyelinase activity. --.

<u>Column 16,</u>
Line 26, please delete "chromogen 3,'diamonobenzidine tetrachloride" and substitute therefor -- chromogen 3,3'-diaminobenzidine tetrachloride --.

UNITED STATES PATENT AND TRADEMARK OFFICE
CERTIFICATE OF CORRECTION

PATENT NO.    : 6,274,309 B1
DATED         : August 14, 2001
INVENTOR(S)   : Kolesnick et al.

It is certified that error appears in the above-identified patent and that said Letters Patent is hereby corrected as shown below:

Column 20,
Line 50, please delete "of step c., or" and substitute therefor -- of step c, or --.
Line 52, please delete "the test compound represents-a compound which increases a: cell-'s-sensitivity to" and substitute therefor -- the test compound represents a compound which increases a cell's sensitivity to --.

Column 21,
Line 29, please delete "apoptosis, comprising," and substitute therefor -- apoptosis, comprising: --.

Column 22,
Line 18, please delete "apoptosis, comprising," and substitute therefor -- apoptosis, comprising: --.

Signed and Sealed this

Twenty-fourth Day of December, 2002

JAMES E. ROGAN
*Director of the United States Patent and Trademark Office*